(12) United States Patent
Sollmann et al.

(10) Patent No.: US 9,999,324 B2
(45) Date of Patent: Jun. 19, 2018

(54) LIQUID-DISPENSING PAD

(71) Applicant: MONDI Gronau GmbH, Gronau (DE)

(72) Inventors: Henner Sollmann, Gronau (DE);
Andreas Brueggemann, Vreden (DE);
Steven Marks Neill, Leeds West Yorkshire (GB)

(73) Assignee: SURFACESKINS LTD., Leeds (GB)

( * ) Notice: Subject to any disclaimer, the term of this patent is extended or adjusted under 35 U.S.C. 154(b) by 0 days. days.

(21) Appl. No.: 14/940,888

(22) Filed: Nov. 13, 2015

(65) Prior Publication Data
US 2016/0174775 A1 Jun. 23, 2016

(30) Foreign Application Priority Data

Dec. 17, 2014 (EP) ..................... 14198623

(51) Int. Cl.
| | |
|---|---|
| *A47K 5/122* | (2006.01) |
| *A01N 25/34* | (2006.01) |
| *A61L 2/18* | (2006.01) |
| *B65D 65/22* | (2006.01) |
| *A61L 2/235* | (2006.01) |
| *E05B 1/00* | (2006.01) |

(52) U.S. Cl.
CPC ............. *A47K 5/122* (2013.01); *A01N 25/34* (2013.01); *A61L 2/18* (2013.01); *A61L 2/235* (2013.01); *B65D 65/22* (2013.01); *E05B 1/0069* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,600,620 | A * | 7/1986 | Lloyd | A47L 13/17 |
| | | | | 15/104.93 |
| 4,832,942 | A | 5/1989 | Crace | |
| 7,037,569 | B2 | 5/2006 | Curro | |
| 7,722,589 | B2 | 5/2010 | Fitts, Jr. | |
| 8,375,521 | B1 * | 2/2013 | Caron | E05B 1/0069 |
| | | | | 16/431 |
| 9,123,257 | B2 * | 9/2015 | Vicente | G09B 19/0076 |
| 2009/0130005 | A1 * | 5/2009 | Balzano | A61L 2/232 |
| | | | | 422/292 |
| 2011/0111000 | A1 | 5/2011 | Russell | |
| 2015/0117932 | A1 * | 4/2015 | Russell | A61L 2/18 |
| | | | | 401/196 |

FOREIGN PATENT DOCUMENTS

EP        2098664 A    9/2009

* cited by examiner

*Primary Examiner* — David Walczak
(74) *Attorney, Agent, or Firm* — Andrew Wilford

(57) ABSTRACT

A liquid-dispensing pad has a perforated generally elastic film forming a front wall, a liquid-impervious plastic rear wall, a weld peripherally securing the front wall to the rear wall, and a liquid-retaining core between the front and rear walls. The perforated film is a coextruded film having an elastic inner layer turned toward the core and an inelastic outer cover layer turned away from the core. This cover layer forms an outer face of the liquid-dispensing pad and is composed of polyolefin. A thickness of the cover layer is less than 15 μm, and a thickness ratio of the elastic inner layer to the inelastic outer cover layer is at least 10:1.

15 Claims, 2 Drawing Sheets

LIQUID-DISPENSING PAD

FIELD OF THE INVENTION

The present invention relates to a liquid-dispensing pad comprising a liquid-impervious rear wall of plastic, a front wall formed by a perforated elastic film that is connected to the rear wall by a thermal weld and a liquid-retaining core between the front and rear wall.

The present invention relates particularly to liquid-dispensing pads that contain a fluid in the form of a disinfecting liquid or gel, where the liquid or the gel can be discharged through the front wall over a long period of time.

BACKGROUND OF THE INVENTION

In order to avoid the transmission of bacteria, pathogenic agents, or the like, such a liquid-dispensing pad can be is mounted on swing doors, door openers, or other devices such as switches where the liquid-dispensing pad, which is also to be referred to as a pad, forms the contact face to be touched by a user.

Thus, such a contact face can be kept free of germs, bacteria, or pathogenic agents by the liquid-dispensing pad, even if the contact face is touched by a large number of users. Furthermore, another resulting advantage is that the user body parts engaging the contact face, such as fingers in particular, can also be wetted with disinfectant to a certain extent so that these parts of the body also can be cleaned to a certain extent.

Thus, the use of such a liquid-dispensing pad having a disinfecting fluid is advantageous particularly where an increased risk of disease transmission exists. In addition to all places having high numbers of staff, such as retail stores, restaurants, and office buildings, the use of the liquid-dispensing pad is also advantageous, for example, in the field of hospitals or also on cruise ships in order to avoid the spread of diseases.

In order to achieve good usage characteristics of the liquid-dispensing pad, various specifications must be taken into consideration. First, the liquid-dispensing pad should be able to accommodate a sufficient amount of fluid in order to also enable use over a long period of time. It should also be avoided that the fluid escapes or evaporates in an uncontrolled manner and, to the extent possible, is released only when the liquid-dispensing pad is used. According to the invention, the elastic, perforated film is provided for this purpose, and the perforations are formed preferably by slits that have a certain valve action. In the undeformed state of the elastic film, the slits of the perforation are only small, or preferably are closed by the material's elasticity. However, when the elastic film, as the front wall of the liquid-dispensing pad, is deformed by the pressure of a user during use, the slits can open locally and fluid is then discharged.

Because the accommodation amount of the liquid-dispensing pad is limited and soiling also cannot be ruled out over a long period time, the liquid-dispensing pad should also be easy to replace, and such a disposable product must then be economical and easy to manufacture.

Furthermore, the front wall, as a contact face, forms the visible top side of the liquid-dispensing pad. In many cases, it should be indicated to a user that only the liquid-dispensing pad should be used as a contact face. Therefore, the front wall generally is printed on, and the print should be both permanent and of high quality and can also be used for advertising purposes.

Liquid-dispensing pads having the features described at the beginning are known from WO 2013/167746 and US 2011/0111000. Furthermore, similar pads provided with a disinfecting material are described in U.S. Pat. Nos. 4,832,942, 7,037,569, 7,722,589, and EP 2,098,664.

In the case of the known designs, the printability of the front wall is in need of improvement.

OBJECTS OF THE INVENTION

It is therefore an object of the present invention to provide an improved liquid-dispensing pad.

Another object is the provision of such an improved liquid-dispensing pad that overcomes the above-given disadvantages, in particular that is effective, has a long service life, and is inexpensive to manufacture.

SUMMARY OF THE INVENTION

The instant invention is an improvement on a liquid-dispensing pad having a perforated generally elastic film forming a front wall, a liquid-impervious plastic rear wall, a weld peripherally securing the front wall to the rear wall, and a liquid-retaining core between the front and rear walls. According to the invention the perforated film is a coextruded film having an elastic inner layer turned toward the core and an inelastic outer cover layer turned away from the core. This cover layer forms an outer face of the liquid-dispensing pad and is composed of polyolefin. A thickness of the cover layer is less than 15 µm, and a thickness ratio of the elastic inner layer to the inelastic outer cover layer is at least 10:1.

The cover layer of polyolefin can be easily printed on, to which end the cover layer is preferably subjected to a corona treatment. However, the cover layer can be formed by coextrusion so thin that the elastic properties of the perforated elastic film, which are provided by the elastic layer, are not significantly impaired. In particular, the cover layer is provided only on the side that forms the contact face and that thus forms the surface of the liquid-dispensing pad. In contrast, the opposite side, which is connected to the rear wall, is formed of an elastic material by the elastic layer in the case of an embodiment of the coextruded film preferably having exactly two layers.

The thickness ratio of the elastic layer to the cover layer is at least 10:1. Good elastic properties and sufficient flexibility of the elastic film are also achieved by this pronounced asymmetry, and the thin cover layer does not significantly impair these properties yet ensures good printability.

Even if the thin, inelastic layer causes a certain stiffness, the pores or slits formed by the perforation can be closed on the side facing inward toward the core at least by the asymmetry of the coextruded film. Slight stiffening at the cover layer to be printed on is even advantageous with regard to the processing of the elastic film, because the elastic film stretches less during the processing of the elastic film and particularly during printing. In this context, the present invention is based on the discovery that the purpose of the elastic layer is not, as is common, good elastic extensibility of the entire front wall but rather local closure of the pores formed by the perforation.

The elastic film preferably can be elongated by at least 50% from a starting length, and when the force applied for the elongation is removed, the permanent deformation in comparison with the initial length is typically less than 20%, preferably less than 10%.

According to the invention, the cover layer, which is composed of polyolefin and preferably is treated by corona discharge, is typically printed on or can be printed on. In particular, polyethylene and polypropylene are considered as a material for the cover layer, and a mixture of polypropylene (PP) and polyethylene (PE) is especially preferred. For example, the concentration of polyethylene in the cover layer can be between 40 and 70 wt % and the concentration of polypropylene can be between 30 and 60 wt %, and talc, processing aids, or further additives can be provided as further components at a concentration of preferably less than 10 wt %.

Preferred polyolefins for the cover layer are linear low-density polyethylene (LLDPE) and polypropylene copolymer.

According to an especially preferred embodiment of the invention, the cover layer also contains an absorber for low-molecular-weight components, such as water and styrene.

Because the elastic film is formed by coextrusion, the cover layer can be very thin, and furthermore no additional adhesive layers or the like are necessary in the coextrusion, depending on the material composition. The thickness of the cover layer is preferably less than 10 µm and at least 2 µm, for example, 4 µm.

The elastic layer contains preferably between 20 and 70 wt % of styrene block copolymer (SBC) and between 15 and 50 wt % of ethylene vinyl acetate (EVA). Styrene-butadiene-styrene copolymer (SBS), styrene-ethylene/butylene-styrene copolymer (SEBS), styrene-ethylene/propylene-styrene copolymer (SEPS), and styrene-isoprene-styrene copolymer (SIS), for example, are considered as styrene block copolymers, and SBS is preferred.

Ethylene vinyl acetate (EVA) is particularly advantageous for achieving good weldability with respect to the rear wall if the rear wall is made of polyethylene terephthalate (PET) according to a preferred embodiment of the invention. For this purpose, the vinyl acetate content in the ethylene vinyl acetate furthermore lies above 10% and preferably above 15%. The vinyl acetate content in the ethylene vinyl acetate can be, for example, 10% to 30%, preferably between 15% and 25%.

The rear wall usually is of shell shape, and the rear wall can be formed in particular by a deep-drawn shell, and polystyrene (PS) and polystyrene copolymer, for example, are also considered as a material in addition to PET. The front wall formed by the elastic film is then preferably welded to a peripheral, bent rim of the shell and covers the cavity formed by the shell and the core in the cavity. In such an embodiment, the elastic film can be substantially flat or only slightly domed, so that the elastic film is then largely undeformed in the unloaded state, for which reason the perforation having a type of valve function can be closed also at the edges because of the elastic properties. In principle, it is also possible to arrange the perforation only in part of the front wall; for example, a lower edge or a peripheral edge have no perforations.

Preferably, the elastic film is perforated by slits, and the slits have a valve function and are at least largely or preferably completely closed in the undeformed state of the elastic film.

With regard to a concrete embodiment of the liquid-dispensing pad, various possibilities are possible according to the invention. As described above, the rear wall can be a stiff, deep-drawn shell, and can be mounted, directly or by a separate support, on the face of a door, of a switch, etc.

Also conceivable, however, are embodiments in which the rear wall is flexible so that the liquid-dispensing pad can be attached to a curved surface such as a grab bar or the like.

The thickness of the elastic layer is typically between 80 µm and 300 µm, preferably between 100 µm and 200 µm, which also corresponds approximately to the total thickness of the elastic film because of the only slight thickness of the cover layer.

As already mentioned above, the liquid of the liquid-dispensing pad is preferably a disinfecting liquid or a disinfecting gel.

In order to be able to retain the fluid, the core advantageously has a suitable body, and the body can be a textile, a nonwoven, wadding, or foam, for example. On the one hand, this material must have pores and free spaces for the fluid. However, on the other hand, certain absorbent properties are advantageous in that the fluid can be retained to a certain extent, so that the fluid is discharged only when the elastic, perforated film is pressed. Furthermore, the body is preferably also elastically compressible to a certain extent.

Finally, the invention also relates to a disinfecting device comprising the liquid-dispensing pad whose rear wall is formed by a deep-drawn shell, and the disinfecting liquid or the disinfecting gel is provided as the liquid. The liquid-dispensing pad is held by a support in such a way that the liquid-dispensing pad can be replaced. Such a support can be formed by a deep-drawn shell, which is then permanently fastened to a contact face, while the liquid-dispensing pad itself can be easily replaced. The support can be, for example, a deep-drawn shell of polyethylene terephthalate.

If both the support and the rear wall of the liquid-dispensing pad are formed as a deep-drawn shell, the rear wall also can be detachably held in the support in a simple manner by a type of fastener.

BRIEF DESCRIPTION OF THE DRAWING

The above and other objects, features, and advantages will become more readily apparent from the following description, reference being made to the accompanying drawing in which.

SPECIFIC DESCRIPTION OF THE INVENTION

Figure 1:
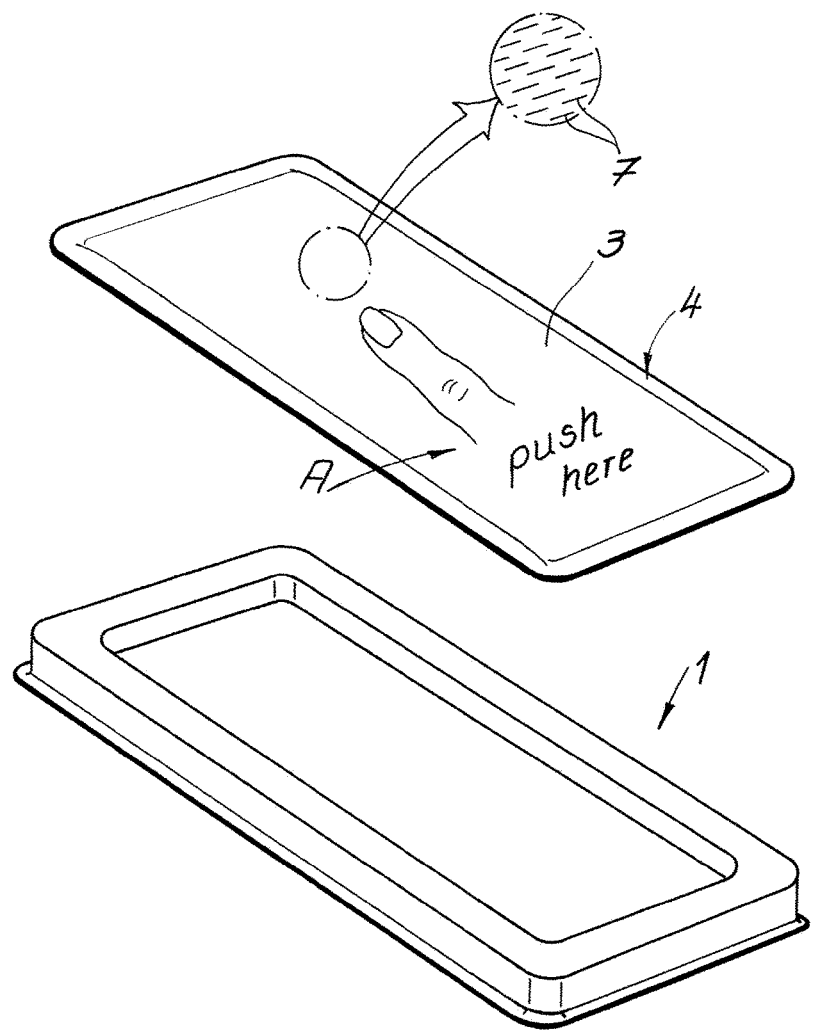
FIG. 1 is a perspective exploded view of a disinfecting device comprising a liquid-dispensing pad and a support.

As seen in FIG. 1 a contact-type liquid-disinfectant dispenser comprises a liquid-dispensing pad and a support 1 for it. The support 1 can be attached to a contact face of a door or the like, and the liquid-dispensing pad then is held on the support 1 by a fastener in such a way that the liquid-dispensing pad can be replaced.

Figure 2:
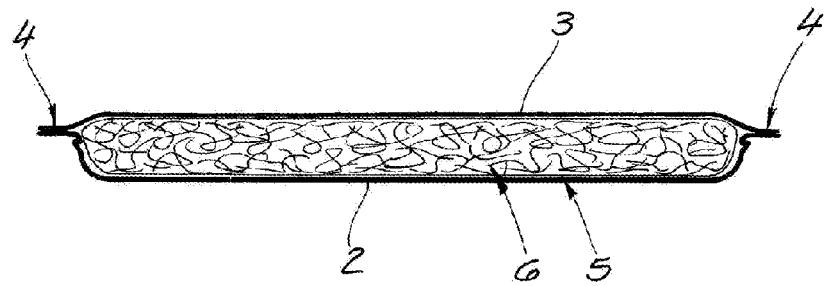
FIG. 2 is a longitudinal section through the liquid-dispensing pad according to FIG. 1.

The details of the liquid-dispensing pad can be seen in the section according to FIG. 2. The liquid-dispensing pad has a liquid-impervious rear wall 2 that is shaped as a shell and is deep-drawn from a PET film. A perforated elastic film 3 is fitted on the opposite front side of the liquid-dispensing pad and is connected to the rim of the wall 2 by a peripheral weld 4. A liquid-retaining core 5 is between the elastic film 3 serving as front wall and the rear wall 2, and the liquid-retaining core has a body 6 made of a textile, nonwoven, wadding, or foam, and the liquid, in the form of a disinfecting liquid or a disinfecting gel is held in the core 5. The body 6 is preferably also elastically compressible, so that, in an undeformed state, the shape of the liquid-dispensing pad seen in FIG. 2 always results.

According to FIG. 1, the perforations are formed by a large number of slits 7 in the elastic film 3. Thus, it is possible that the slits 7 have a valve function because of the elastic properties of the elastic film 3, and the slits 7 are at least largely closed in the undeformed state of the elastic film 3 so that the liquid is held back in the liquid-retaining core 5. When the elastic film 3 is deformed by the touch of a user, the elastic film 3 can then deform in such a way that these slits open and liquid is discharged.

FIG. 1 also shows that the elastic film 3 is provided with printed matter A on the exposed surface. First, the liquid-dispensing pad should have a high-quality appearance, and second, it must also show the user that the liquid-dispensing pad, as part of a disinfecting device, should be used as a contact face.

Figure 3:
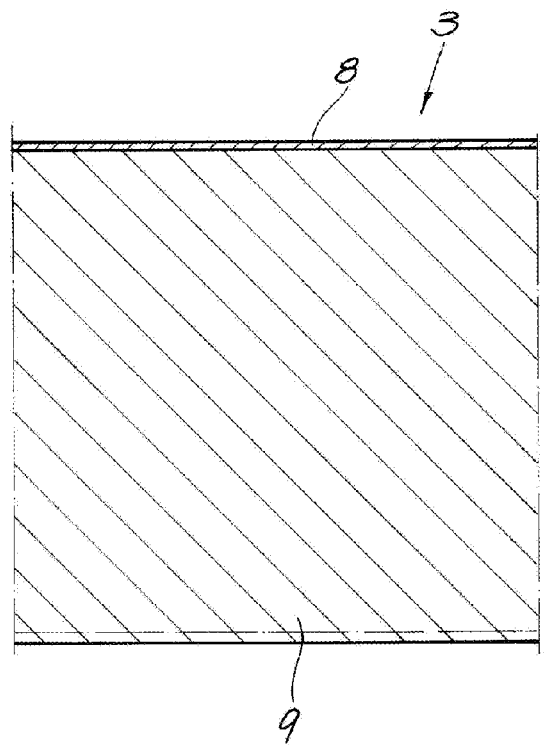
FIG. 3 is a large-scale section through a front wall of the liquid-dispensing pad illustrated in FIG. 2.

According to the invention, as illustrated in FIG. 3, the elastic film 3 is formed by an at least two-layer coextruded film that has an inelastic thin cover layer 8 that forms a surface of the liquid-dispensing pad and is composed of polyolefin, and an elastic layer 9. The elastic layer 9 is on the face toward the liquid-retaining core 5, and the opposite thin cover layer has a thickness of less than 10 μm according to the invention. The thickness ratio of the elastic layer 9 to the cover layer 8 is at least 10:1.

In the illustrated embodiment, the outer layer has a thickness of 4 μm and contains 55 wt % LLDPE, 40 wt % PP copolymer, and the remainder talc, processing aids, and absorber. The absorber is provided specifically for absorbing low-molecular-weight components that can leave the elastic layer 9.

The cover layer is treated by corona discharge in order to improve printability.

The core layer has a thickness of 196 μm in total, and therefore in this embodiment a thickness ratio of 49:1 results.

The elastic layer is composed of 40 wt % SBS and 35 wt % EVA having a vinyl acetate content of 18%. Furthermore, the elastic layer contains processing aids, pigments, lubricants, anti-blocking agents, and stabilizers.

Thus, this is a heavily asymmetric two-layer coextruded film.

In the embodiment according to FIG. 3, this coextruded film, which in itself has two layers, is produced by an extrusion system designed for three layers. For this purpose, the elastic layer 9 is formed of two sublayers having the same material composition, and the sublayer located in the middle of the layer structure has a thickness of 192 μm and the other sublayer has a thickness of 4 μm. However, the layer transition is generally no longer detectable in the coextruded film, because the sublayers melt together during the coextrusion. The layer transition is indicated by a dot-and-dash line in FIG. 3.

Figure 4:
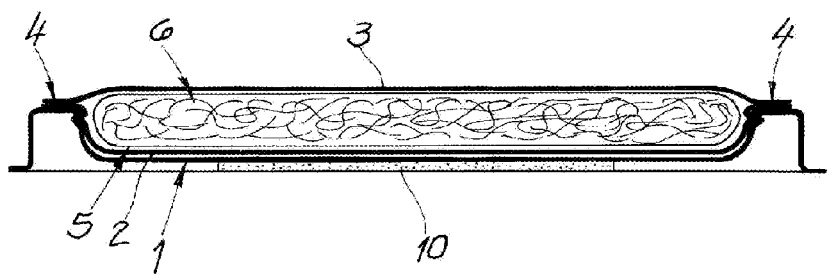
FIG. 4 is a section like FIG. 2, but with the liquid-dispensing pad and the support according to FIG. 1.

Finally, FIG. 4 shows the liquid-dispensing pad held on the support 1 and, for example, secured by a fastener, so that the liquid-dispensing pad can be easily replaced. The support 1 can be fastened, for example by adhesive strips 10, to a face of a door or the like.

We claim:

1. In a liquid-dispensing pad comprising:
a liquid-retaining core layer; and
a perforated, coextruded, and generally elastic film forming a front wall and having an elastic inner layer turned toward the core and inelastic polyolefin outer cover layer turned away from the core and forming an outer face of the liquid-dispensing pad, a thickness of the cover layer being less than 15 μm and a thickness ratio of the elastic inner layer to the inelastic outer cover layer is at least 10:1.

2. The liquid-dispensing pad defined in claim 1, wherein the elastic film is formed with slits that act as valves and are closed in an undeformed state of the elastic film.

3. The liquid-dispensing pad defined in claim 1 further comprising:
printed matter on an outer face of the cover layer.

4. The liquid-dispensing pad defined in claim 1, further comprising a rear wall that is made of polyethylene terephthalate.

5. The liquid-dispensing pad defined in claim 1, further comprising a rear wall formed by a deep-drawn shell having a peripheral bent rim, a weld securing the elastic film to the rim so as to lie substantially in a plane.

6. The liquid-dispensing pad defined in claim 1, wherein the elastic layer contains between 20 wt % and 70 wt % of styrene block copolymer and between 15 wt % and 50 wt % of ethylene vinyl acetate.

7. The liquid-dispensing pad defined in claim 6, wherein the vinyl acetate content in the ethylene vinyl acetate is between 10% and 30%.

8. The liquid-dispensing pad defined in claim 1, further comprising a rear wall to which the elastic layer of the elastic film is welded.

9. The liquid-dispensing pad defined in claim 1, wherein the cover layer contains an absorber for low-molecular-weight components.

10. The liquid-dispensing pad defined in claim 1, wherein the elastic layer has a thickness between 80 μm and 300 μm.

11. The liquid-dispensing pad defined in claim 1, wherein the cover layer has a thickness of at least 2 μm.

12. The liquid-dispensing pad defined in claim 1, wherein the polyolefin of the cover layer comprises a mixture of polypropylene and polyethylene.

13. The liquid-dispensing pad defined in claim 12, wherein the mixture comprises between 40 to 70 wt % polyethylene and between 30 to 60 wt % polypropylene.

14. The liquid-dispensing pad defined in claim 1, wherein the polyolefin of the cover layers comprises linear low-density polyethylene and polypropylene copolymer.

15. In a liquid-dispensing pad comprising:
a liquid-retaining core layer; and
a perforated and generally elastic film forming a front wall, and having an elastic inner layer turned toward the core and coextruded with an inelastic outer layer turned away from the core and forming an outer face of the liquid-dispensing pad, the outer cover layer being thinner than the elastic inner layer.

* * * * *